(12) United States Patent
Fowler-Hawkins

(10) Patent No.: US 6,702,769 B1
(45) Date of Patent: Mar. 9, 2004

(54) DEVICE AND METHOD FOR INDUCING SPUTUM

(75) Inventor: Sanford Elliot Fowler-Hawkins, New York, NY (US)

(73) Assignee: Medical Acoustics, LLC, Buffalo, NY (US)

( * ) Notice: Subject to any disclaimer, the term of this patent is extended or adjusted under 35 U.S.C. 154(b) by 0 days.

(21) Appl. No.: 10/274,715

(22) Filed: Oct. 21, 2002

Related U.S. Application Data

(60) Provisional application No. 60/346,343, filed on Jan. 7, 2002.

(51) Int. Cl.$^7$ .................................................. A61H 1/00
(52) U.S. Cl. ...................... 601/46; 601/47; 128/200.24; 482/13
(58) Field of Search ............................ 601/41, 43, 46, 601/47; 482/13; 128/200.24, 202.28, 202.29, 204.18; 84/363, 402, 410

(56) References Cited

U.S. PATENT DOCUMENTS

| | | | | |
|---|---|---|---|---|
| 1,836,816 A | * | 12/1931 | Riesz | ............ 84/363 |
| 2,599,135 A | * | 6/1952 | Seybold | ............ 84/363 |
| 4,054,134 A | | 10/1977 | Kritzer | |
| 4,062,358 A | | 12/1977 | Kritzer | |
| 4,226,233 A | | 10/1980 | Kritzer | |
| 4,595,004 A | | 6/1986 | Czech | |
| 4,745,910 A | | 5/1988 | Day et al. | |
| 5,167,226 A | | 12/1992 | Laroche et al. | |
| 5,261,394 A | | 11/1993 | Mulligan et al. | |
| 5,569,122 A | | 10/1996 | Cegla | |
| 5,829,429 A | | 11/1998 | Hughes | |
| 5,890,998 A | | 4/1999 | Hougen | |
| 5,893,361 A | | 4/1999 | Hughes | |
| 5,899,832 A | | 5/1999 | Hougen | |
| 5,988,166 A | | 11/1999 | Hayek | |
| 6,053,879 A | | 4/2000 | Leban et al. | |
| 6,058,932 A | | 5/2000 | Hughes | |
| 6,083,141 A | | 7/2000 | Hougen | |
| 6,158,439 A | | 12/2000 | Streetman | |
| 6,167,881 B1 | | 1/2001 | Hughes | |
| 6,176,235 B1 | | 1/2001 | Benarrouch et al. | |
| 6,193,677 B1 | | 2/2001 | Cady | |

FOREIGN PATENT DOCUMENTS

GB      2196858      5/1988

OTHER PUBLICATIONS

Acapella Mucus Clearance Device, found on the Technical Information section of DHD Healthcare's website, http://www.dhd.com/html/techinfo/acapella.html, pp. 1–3, dated Nov. 9, 2001.

Bullock, Robert M., III, *Bullock on Boxes*, Audio Amateur Press, Peterborough, New Hampshire, copyright ©1995.

* cited by examiner

*Primary Examiner*—Danton D. DeMille
*Assistant Examiner*—Quang Thanh
(74) *Attorney, Agent, or Firm*—King & Spalding LLP

(57) ABSTRACT

A device for thinning lung secretions comprises a housing, a reed disposed in the housing, and an acoustical resistance. The reed produces a low-frequency audio shockwave when vibrated. The acoustical resistance couples a patient's lungs to the audio shockwave and creates a back pressure of the low-frequency shockwave into a patient's lungs.

62 Claims, 14 Drawing Sheets

DEVICE AND METHOD FOR INDUCING SPUTUM

PRIORITY AND RELATED APPLICATIONS

This application claims the benefit of priority to U.S. Provisional Patent Application Serial No. 60/346,343, entitled "Lung Cleaning Device," filed Jan. 7, 2002. The complete disclosure of the above-identified priority application is fully incorporated herein by reference.

FIELD OF THE INVENTION

The present invention relates generally to vibrating a patient's lungs to reduce the viscosity of mucus contained therein. More particularly, the present invention relates to a device and method for vibrating a patient's lungs with low-frequency audio shockwaves.

BACKGROUND OF THE INVENTION

The human lungs comprise a natural means for clearing mucus. Human lungs contain tiny clearing cilia that vibrate at approximately 18 Hz. At that frequency, mucus has a significant phase change from a viscous to fluid to thinner secretions. Accordingly, the cilia operate to loosen the mucus by making it more fluid. Once the mucus is more fluid, it can be more easily expelled.

Some patients with weak lungs, disease, or other ailments have lungs that cannot create a sufficient phase change in the viscous mucus. Additionally, a doctor may need to induce a sputum sample from a patient. Accordingly, an artificial means of vibrating the lungs at approximately 18 Hz can be used to supplement the patient's natural mucus system. In some cases, an artificial means of vibrating the lungs can produce the same phase change in mucus as produced by the lungs' natural cilia.

One conventional method for artificially vibrating a patient's lungs is by using pulses of air pressure introduced through the mouth and into the lungs. However, such a method can produce dangerously high air pressures, which can damage the fragile air sacs in the lungs.

Another conventional method for artificially vibrating a patient's lungs is by using low frequency audio of approximately 18 Hz to make lung secretions thinner. Low frequency audio does not induce potentially dangerous high air pressures in the lungs that are associated with the air pulses discussed above. However, conventional methods require very high audio power to cause vibration at low frequencies. Common loudspeaker components can be used to provide a high-powered audio source for vibrating the lungs. However, the life expectancy of the high-powered audio drivers is low, and the cost of the high-powered audio drivers is high. Additionally, powered subwoofers and loudspeakers typically are not disposable or portable.

A patient's lungs and vocal cords make a particularly efficient loudspeaker in the vocal range. However, low frequencies are not efficiently produced because both the vocal cords and the lungs are too small. If the lungs could be made larger, they would support low frequency audio production, and they also would couple efficiently to a low frequency audio source.

Therefore, a need in the art exists for a system and method that can provide a low-cost, disposable, and/or portable, artificial means of vibrating a patient's lungs to cause a viscous change in mucus contained therein. A need in the art also exists for an efficient means of coupling a patient's lungs with an audio source to produce a low frequency vibration in the lungs. Additionally, there exists a need in the art for a non-powered, low-frequency audio source for artificially vibrating a patient's lungs.

SUMMARY OF THE INVENTION

The present invention can provide a device and method for artificially vibrating a patient's lungs to cause a viscosity change in mucus contained therein. The device and method can be used to clean mucus from the lungs or to induce a sputum sample for diagnostic purposes from the lungs.

The lung vibrating device and method according to the present invention can allow the lungs to produce low frequency audio that can vibrate the lungs at the desired frequency to change the viscosity of mucus. Typically, human lungs are too small to produce low-frequency audio sound. The lung vibrating device and method according to the present invention can comprise an acoustical resistance that can increase the apparent volume of the lungs, thereby allowing the lungs to produce low-frequency audio in the desired range. The acoustical resistance can allow the lungs to couple efficiently to an audio source to produce low-frequency shockwaves. The acoustical resistance can make the audio source behave as if it is operating in a much larger volume than the body cavity alone, thereby allowing low-frequency audio to be produced and considerably improving energy transfer efficiency. The present invention can generate relatively low frequencies efficiently by using an acoustical coupling technique based on Thiele-Small loudspeaker parameters.

The device according to the present invention can use the acoustical resistance to improve the transfer of audio energy to a body cavity such as the lungs. The device can produce low frequency audio and then can use the body cavity as a loudspeaker enclosure. The acoustical resistance can couple the body cavity efficiently to the low frequency sound. Additionally, the acoustical resistance can efficiently couple the sound/audio/shockwave to the body cavity to vibrate the lungs at the desired frequency. Accordingly, small and inexpensive sound sources can efficiently generate low frequency audio in body cavities.

In an exemplary aspect of the present invention, a lung vibrating device can comprise a reed disposed in a housing. A patient can blow air through the housing, which can cause the reed to vibrate and produce an audio shockwave. An acoustical resistance of the device can couple the audio shockwave produce by the reed with the lungs to produce low-frequency vibrations. Accordingly, the acoustical resistance can provide a back pressure that can transmit the low-frequency vibrations into the lungs to cause a viscosity change in mucus.

These and other aspects, objects, and features of the present invention will become apparent from the following detailed description of the exemplary embodiments, read in conjunction with, and reference to, the accompanying drawings.

DETAILED DESCRIPTION OF EXEMPLARY EMBODIMENTS

Figure 1A:
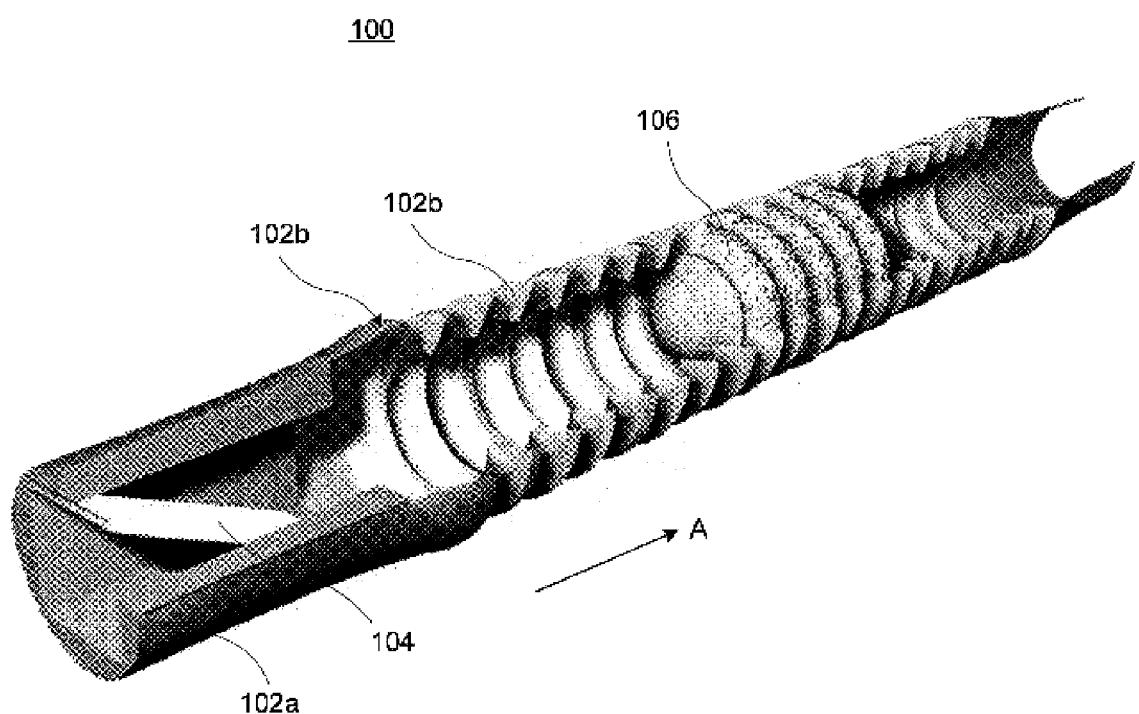
FIG. 1A illustrates a perspective, cut-away view of a lung vibrating device according to an exemplary embodiment of the present invention.

Exemplary embodiments of the present invention will be described below with reference to FIGS. 1–12 in which the same reference numerals represent similar elements.

Figure 1B:
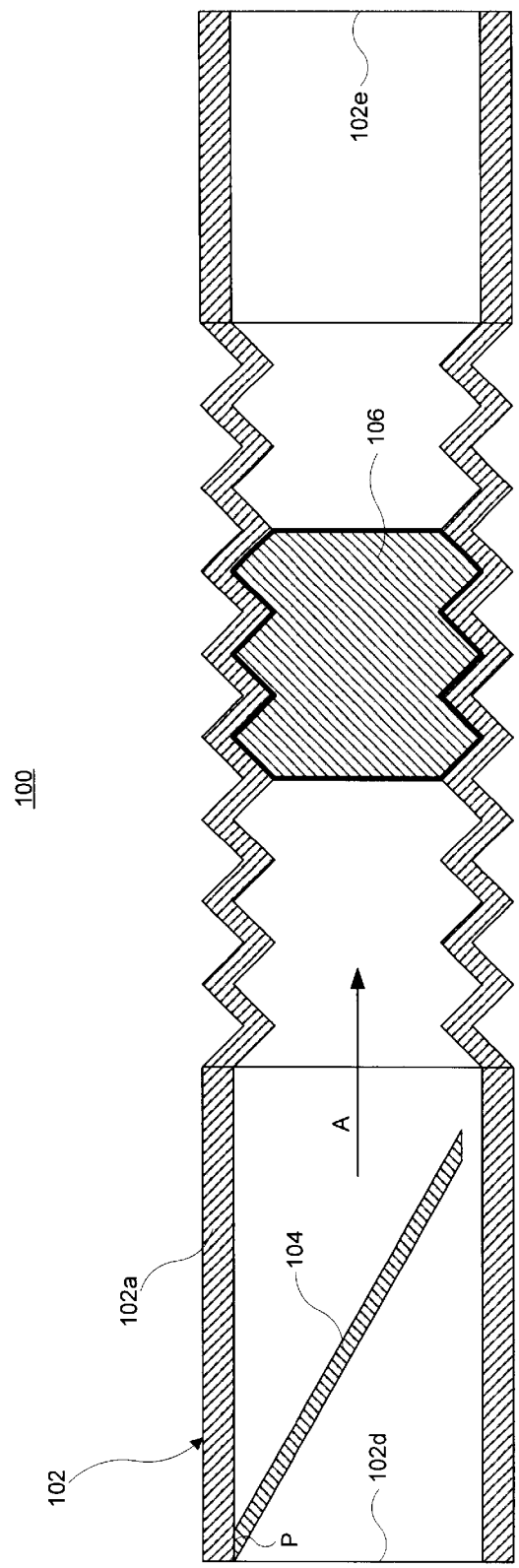
FIG. 1B illustrates a cross-sectional, side view of the exemplary lung vibrating device illustrated in FIG. 1.

FIG. 1A illustrates a perspective, cut-away view of a lung vibrating device 100 according to an exemplary embodiment of the present invention. FIG. 1B illustrates a cross-sectional, side view of the exemplary lung vibrating device 100. The device 100 comprises an unpowered, disposable audio noisemaker. As shown in FIGS. 1A and 1B, the device 100 comprises a harmonica-type, free reed 104 in a housing 102. The device 100 also comprises an acoustical resistance 106 disposed within the housing 102.

The housing 102 can comprise a standard respiratory tube or other suitable material. As shown, the reed 104 can be coupled at point P to an insert 102a disposed in the housing 102. Alternatively, the reed 104 can be provided in a separate end cap (not shown) that couples to an end of the housing 102. The reed 104 can be coupled to the housing 102, or to the housing insert 102a, by any suitable method. For example, the reed 104 can be glued or sonically welded to the housing 102 or insert 102a.

The reed 104 can be formed from any suitable material such as plastic, wood, or metal, or combinations of those materials. In one exemplary embodiment, the reed 104 can be formed of solid brass. In another exemplary embodiment, the reed 104 can be formed of Mylar. In another exemplary embodiment, the reed 104 can be a composite of several materials. For example, the reed 104 can be formed of two Mylar sheets with an inner stiffening material. The stiffening material can be any suitable material, for example, tin foil.

The efficiency of the reed 104 can be increased by providing a weight (not shown) on its free end. For a more complete discussion of weighting the free end of the reed, see the discussion below with reference to FIGS. 9A–9F. The weight can assist the reed 104 in vibrating as air flows past it. Alternatively or additionally, the efficiency of the reed 104 can be increased by providing an airfoil (not shown) on its free end. As air flows past the reed 104, the airfoil provides lift, which cause the free end of the reed 104 to rise. As the airfoil rises with the free end, the airfoil stalls, causing the reed 104 to fall.

Because the lung clearing cilia of most patients operate at approximately 18 Hz, the device 100 does not need to reproduce a wide frequency range of sound. Accordingly, in an exemplary embodiment, the device 100 can be tuned to an operating frequency of about 18 Hz, or it can be tuned to match the operating frequency of a specific patient's cilia. Matching the acoustical resistance of the device to the patient's lung cavity can make the device efficient and inexpensive. In an alternative exemplary embodiment, the device can be tuned to operate in a frequency range of about 12 Hz to about 24 Hz. In another alternative exemplary embodiment, the device can be tuned to operate in a frequency range of about 16 Hz to about 20 Hz.

Regarding the vibration frequency of the device, a reed can be tuned to vibrate at the desired frequency. Alternatively, a process called sub-harmonic doubling can be used. In that process, the reed can be tuned to vibrate at a frequency that is about double the desired frequency. However, in sub-harmonic doubling, an additional shockwave is produced at about one-half of the vibration frequency. Accordingly, the additional shockwave is produced at about the desired frequency. For example, the reed can be tuned to vibrate at about 36 Hz, thereby producing an additional shockwave at the desired frequency of about 18 Hz.

In an exemplary embodiment of the present invention, the acoustical resistance 106 can comprise a small piece of foam, a medical HEPTA filter of the desired acoustical resistance, or a cone tapering down to a smaller diameter. In another alternative exemplary embodiment, a variable acoustical resistance can be used to tune the system to a particular patient. For example, the acoustical resistance 106 can be a variably compressed piece of foam, interchangeable HEPTA filters having different resistances, or a variable shutter or valve giving an adjustable exit diameter. Alternatively, the acoustical resistance 106 can be replaced with a movable piston (not shown) disposed on the exit end of the housing 102. The movable piston can control the amount of resistance provided to air exiting the housing 102.

To use the device 100 for lung cleaning or sputum sample induction, a patient exhales through the housing 102 of the device 100 for about 3 minutes or less. As the patient exhales through the housing 102, air enters the housing in the direction A through end 102d of the housing 102 and exits the housing 102 and end 102e. The air passing by reed 104 causes the reed 104 to vibrate. The reed 104 can be tuned to vibrate at about 18 Hz (or to a frequency corresponding to the patient's cilia). The device can produce a volume of about 10 dBa to about 75 dBa. In alternative exemplary embodiments, the device can be tuned to produce a volume of about 10 dBa to about 20 dBa or about 65 dBa to about 75 dBa. The pressure resistance produced can be about 2.5 cm $H_2O$ at 100 Lpm. In terms of pressure or power, 70 dBa is about three orders of magnitude less than typical activities such as yelling or loud continuous coughing.

While the device 100 only applies about between about 75 to about 100 dBa to the airway, it can drive the thorax hard enough to feel the lungs vibrate through thick clothing. By vibrating the lungs at approximately 18 Hz, the lung secretions can become thinner, allowing the natural cleaning action of the lung's mucus pump to dispose of the secretions. After using the device 100, the secretions collect at the back of the patient's throat for approximately 3 to 12 hours. The patient then can swallow the secretions or orally expel them.

Figure 2:
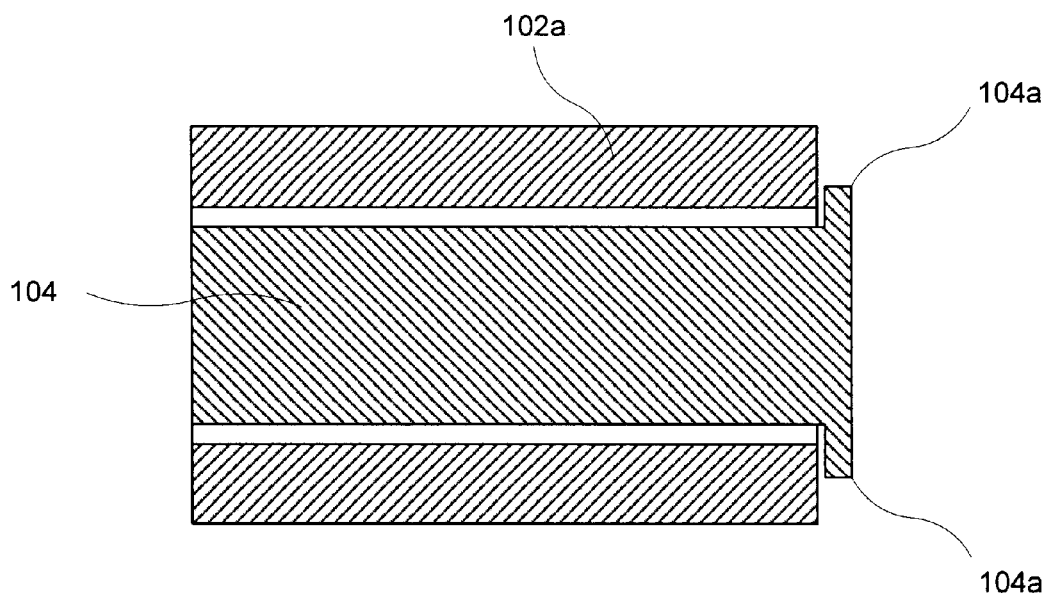
FIG. 2 is a cross section of an exemplary housing insert illustrating an exemplary embodiment of a reed disposed in a housing.

FIG. 2 is a cross section of an exemplary housing insert 102a illustrating an exemplary embodiment of the reed 104 disposed in the housing 102. To prevent the reed 104 from breaking off and being swallowed by a patient (for a patient using the proper end of the device 100 but inhaling too hard through the device), a free end 104a of the reed 104 can be made large enough that it will not fit through the end of the housing insert 102a and into the lungs.

If the device 100 is used backwards and the reed vibrates when a patient inhales, lung secretions can be driven deeper into the lungs. In an exemplary embodiment, to prevent a patient from using the device 100 backwards and vibrating the reed 104 while inhaling, one or more holes (not shown) can be provided in the housing 102 between the acoustical resistance 106 and the exit end 102e of the housing 102. The hole(s) can allow enough air to enter the housing 102 to prevent the reed 104 from vibrating. If a hole is provided in the reed end of the housing 102, it can be provided between the reed 104 and the acoustical resistance 106.

A powered system (not shown) using the non-powered disposable device 100 also can be encompassed by the present invention. An exemplary powered system can comprise an external voice coil that drives the reed 104 with a small steel element added to the tip of the reed 104. The coil can be activated alternately to vibrate the reed 104. Some potential applications such as an intensive care unit ("ICU") or neonatal lung cleaning may require an externally powered system if the patient is unable to exhale through the device. Additionally, a powered system can be useful with unconscious patients or patients with excessive lung secretions or extensive scarring. Another advantage of the powered system according to the present invention is that all parts in contact with the patients are disposable.

A powered system should not be used while inhaling, as the lung secretions can be driven deeper into the lungs. To prevent operation of the system while inhaling, the powered system can comprise a pressure sensitive flap in the housing 102 that opens on inhale, thereby reducing the acoustical coupling and the low frequency efficiency below that necessary to cause vibration of the reed 104.

The unpowered lung vibrating device 100 also can include the intake flap described above. However, the flap may not be necessary on the unpowered device, because the reed may not vibrate on inhale and the reed seal makes it difficult to inhale (if the user is blowing through the right end of the device).

Figure 3:
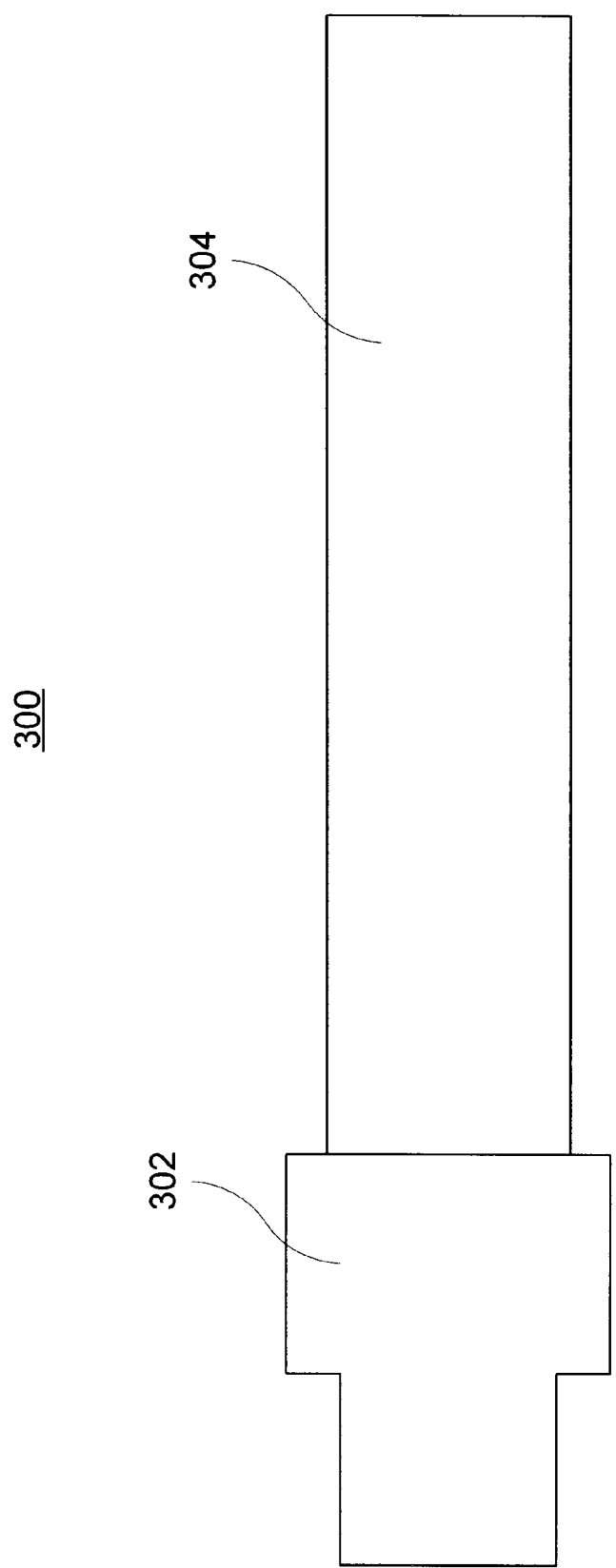
FIG. 3 is a side view illustrating a lung vibrating device according to an alternative exemplary embodiment of the present invention.
Figure 4:
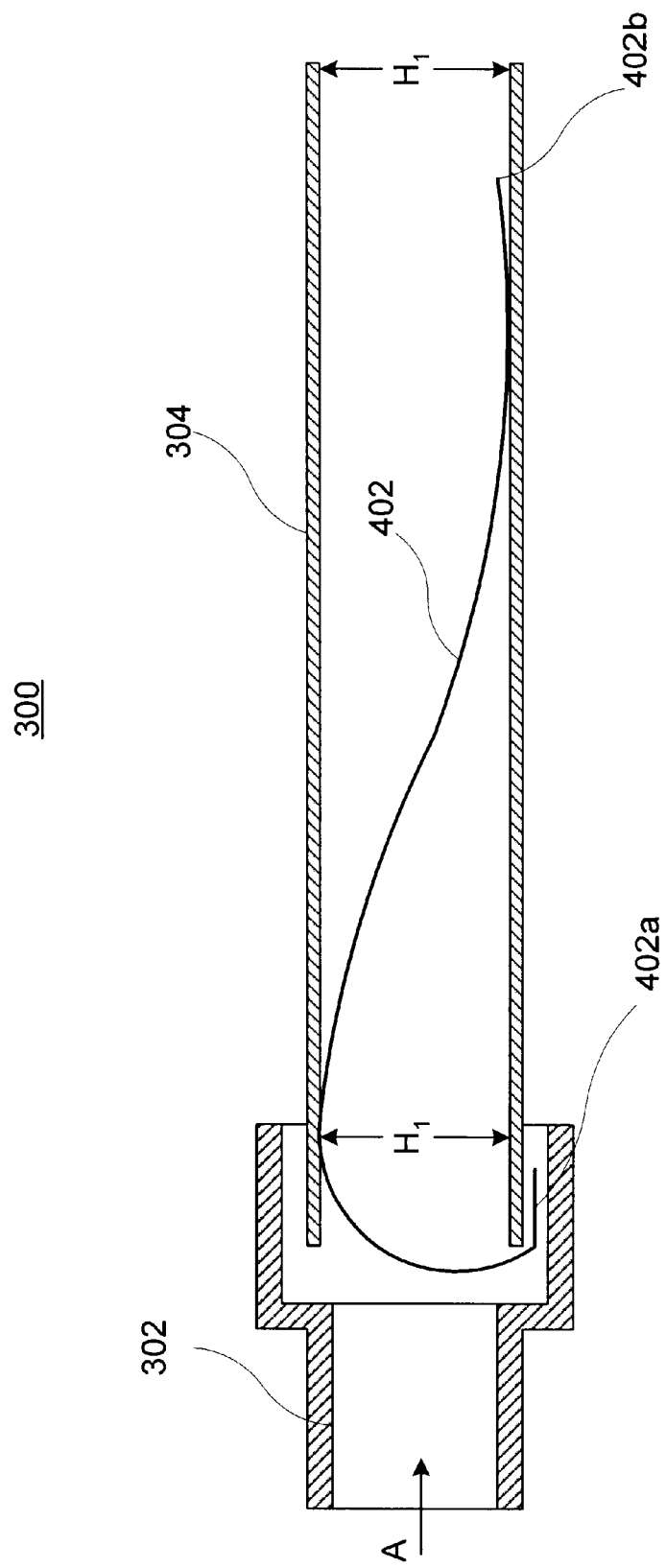
FIG. 4 is a cross-sectional view of the exemplary lung vibrating device illustrated in FIG. 3.

FIG. 3 is a side view illustrating a lung vibrating device 300 according to an alternative exemplary embodiment of the present invention. FIG. 4 is a cross-sectional view of the exemplary lung vibrating device 300 illustrated in FIG. 3. As shown, the lung vibrating device 300 comprises a first end cap 302 coupled to a housing 304. The housing 304 can comprise a substantially uniform cross section, as indicated by the substantially equal heights $H_1$.

The first end cap can comprise a mouth piece through which a patient blows air in the direction A into the housing 304. A reed 402 is disposed within the housing 304. The reed 402 comprises a fixed end 402a and a free end 402b. As shown in the exemplary embodiment of FIG. 4, the fixed end 402a can be compression or friction fitted between the first end cap 302 and the housing 304. In an exemplary embodiment, one of the housing 304 and the end cap 302 can comprise a positioning channel (not shown) that positions the reed 402 along a center of the housing 304. In another exemplary embodiment, one of the housing 304 and the end cap 302 can comprise ribs (not shown) that contact the fixed end 402a of the reed 402 to hold the reed 402 in place. In another exemplary embodiment, the fixed end 402a of the reed 402 can comprise a T-shape (not shown) that extends outside the end cap 302. The T-shape can maintain the reed 402 at the proper position within the housing 304 by preventing the reed 402 from slipping into the housing 304.

In alternative exemplary embodiments (not shown), the fixed end 402a of the reed 402 can be glued, sonically welded, or taped to either the end cap 302 or the housing 304. Any suitable method-for coupling the reed to the device is within the scope of the present invention. In an exemplary embodiment, an entrance opening of the end cap 302 can be small enough to prevent the reed from exiting the device and being inhaled by a patient. In an alternative exemplary embodiment, the end cap 302 can comprise vanes (not shown) that reduce the open area of the end cap 302 to prevent the reed from passing therethrough.

The housing 304 can comprise a rectangular or square shape to minimize air flow around the reed 402. However, the present invention is not limited to only those shapes and encompasses other shapes. For example, the housing 204 can be circular, oval, or any other suitable shape. Those shapes may incur a slight efficiency drop, which can be compensated for by adjusting the acoustical resistance of the device.

The reed 402 can comprise any material having a suitable stiffness that will not absorb excessive energy from the vibrations. For example, the reed 402 can comprise plastic, wood, bone, metal, or combinations of those materials. In an exemplary embodiment, the reed 402 can comprise Mylar. The Mylar thickness can be in a range of about 3.75 mils to about 10 mils. In the exemplary embodiment of FIG. 4, the reed comprises Mylar having a thickness of about 5 mils and a length of about 12.25 inches.

The end cap 302 can be shaped externally to allow a patient' mouth to achieve a suitable seal around the end cap 302. For example, the end cap 302 can have a circular or oval external shape. Other external shapes that achieve a suitable seal are within the scope of the present invention. For example, the external shape can be square or rectangular.

The end cap 302 can be coupled to the housing 304 by various methods. In an exemplary embodiment, the end cap 302 can be glued or sonically welded to the housing 302. In an alternative exemplary embodiment, the end cap 302 can be compression or friction fitted onto the housing 304. In another alternative exemplary embodiment, the end cap 302 can interlock with the housing 304 through the use of a hook and latch or other suitable type of clipping device. In any case, the end cap 302 can be coupled to the housing 304 such that the air moving in direction A will not leak between the end cap 302 and the housing 304 in an amount sufficient to reduce the effectiveness of the device 300.

In an alternative embodiment (not shown), the housing 304 can be suitably shaped on its entrance end to perform the function of a mouthpiece. In that embodiment, the end cap 302 can be omitted.

Figure 5:
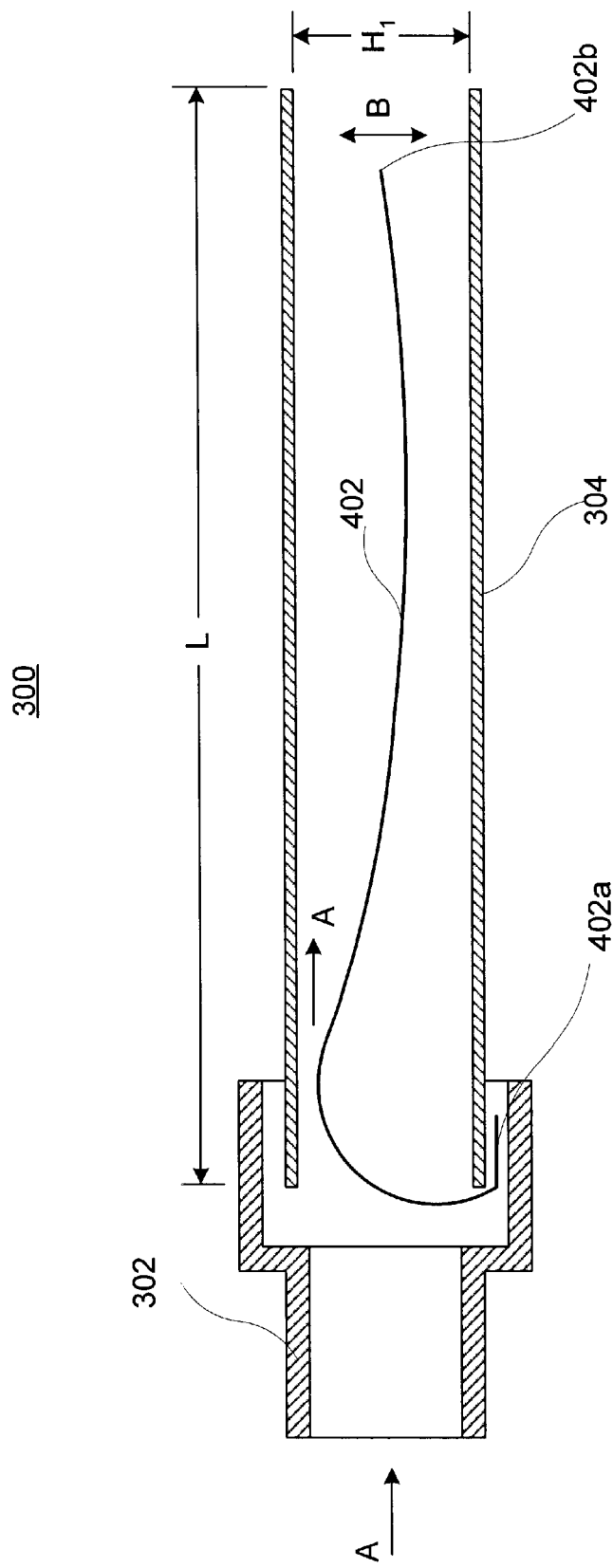
FIG. 5 is a cross-sectional view illustrating an operation of a lung vibrating device according to an exemplary embodiment of the present invention.

FIG. 5 illustrates a cross-sectional view of the lung vibrating device 300 in operation according to an exemplary embodiment of the present invention. In operation, a patient blows air in the direction A into the first end cap 302. As the air passes in the direction A over the reed 402, the free end 402b of the reed 402 vibrates up and down, as indicated by the arrow B. The vibration produces an acoustical shockwave within the housing 304.

An acoustical resistance in the device 300 couples the patient's lungs to the acoustical shockwave to allow production of low-frequency audio shockwaves. The acoustical resistance provides a back pressure of the acoustical shockwave back through the end cap 302 and into the patient's lungs. In the exemplary embodiment illustrated in FIGS. 4 and 5, the acoustical resistance can comprise an air mass provided in the housing 304. In that exemplary embodiment, a length L and the height $H_1$ of the housing 304 can comprise a volume sufficient to provide an air mass large enough to produce the desired acoustical resistance (and back pressure).

Additionally or alternatively, a size or compliance of the reed 402 can provide the acoustical resistance. For example, the size or compliance of the reed 402 can be increased until the amount of air required to vibrate the reed 402 is sufficient to provide the desired acoustical resistance and back pressure into the patient's lungs.

Figure 6:
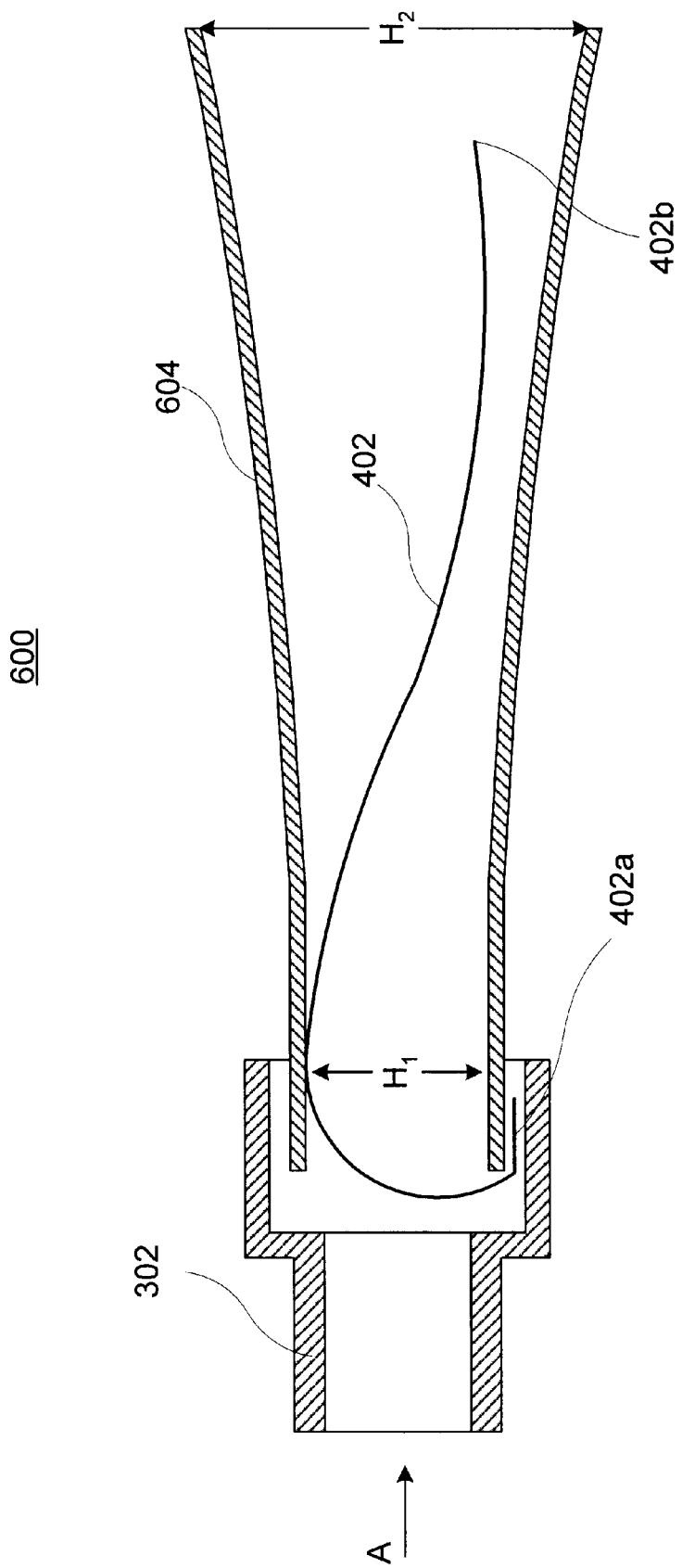
FIG. 6 illustrates a cross-sectional view of a lung vibrating device according to an alternative exemplary embodiment of the present invention.

FIG. 6 illustrates a cross-sectional view of a lung vibrating device 600 according to an alternative exemplary embodiment of the present invention. As shown, the device 600 comprises the first end cap 302 and a housing 604. The reed 402 is disposed within the housing 604. The housing 604 can have a horn shape, whereby a first portion has a height $H_1$ and a second portion has a height $H_2$, which is larger than the height $H_1$. Accordingly, a cross-sectional area of the first portion is less than a cross sectional area of the second portion. In operation, the free end 402b of the reed 402 vibrates up and down in the second portion of the housing 604. Accordingly, the free end 402b has additional space to vibrate up and down. Additionally, the free end 402b is less likely to contact the housing 604. The horn shape also increase the air flow through the device. The increased air flow can have several benefits. For example, the increased air flow can provide additional air that reduces fogging of the housing by drying condensation that forms on the housing. Additionally, the increased volume can increase the acoustical resistance of the device.

Figure 7:
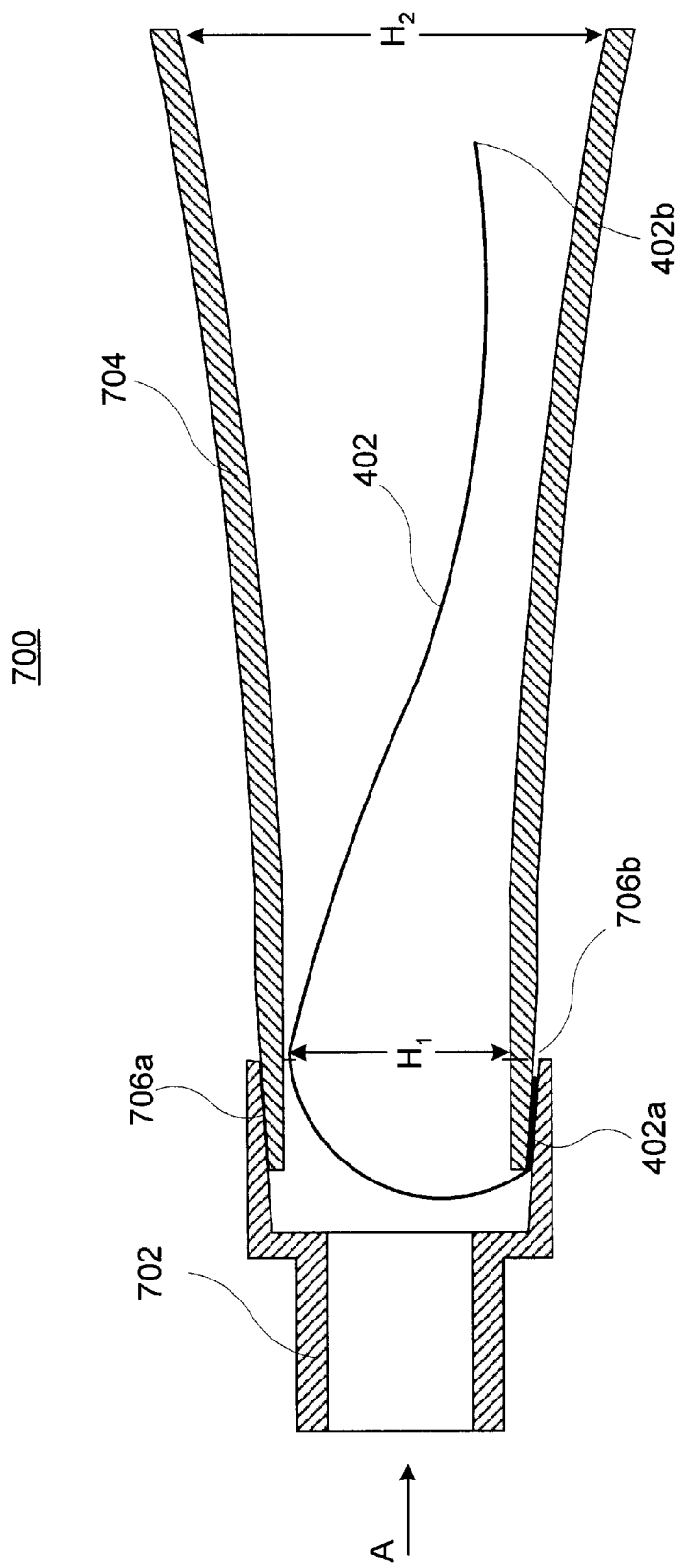
FIG. 7 illustrates a cross-sectional view of a lung vibrating device according to another exemplary embodiment of the present invention.

FIG. 7 illustrates a cross-sectional view of a lung vibrating device 700 according to another exemplary embodiment of the present invention. As shown, the device 700 comprises an end cap 702 and a housing 704. The device 700 also comprises the reed 402 disposed in the housing 704. The end cap 702 and the housing 704 can have correspondingly tapered ends 706a, 706b. The tapered ends can provide an improved compression fit between the end cap 702 and the housing 704. Additionally, the tapered ends 706a, 706b can prevent drawing and excessive amount of the fixed end 402a of the reed 402 out of the housing 704 as the end cap 702 and the housing 704 are pushed together.

Figure 8:
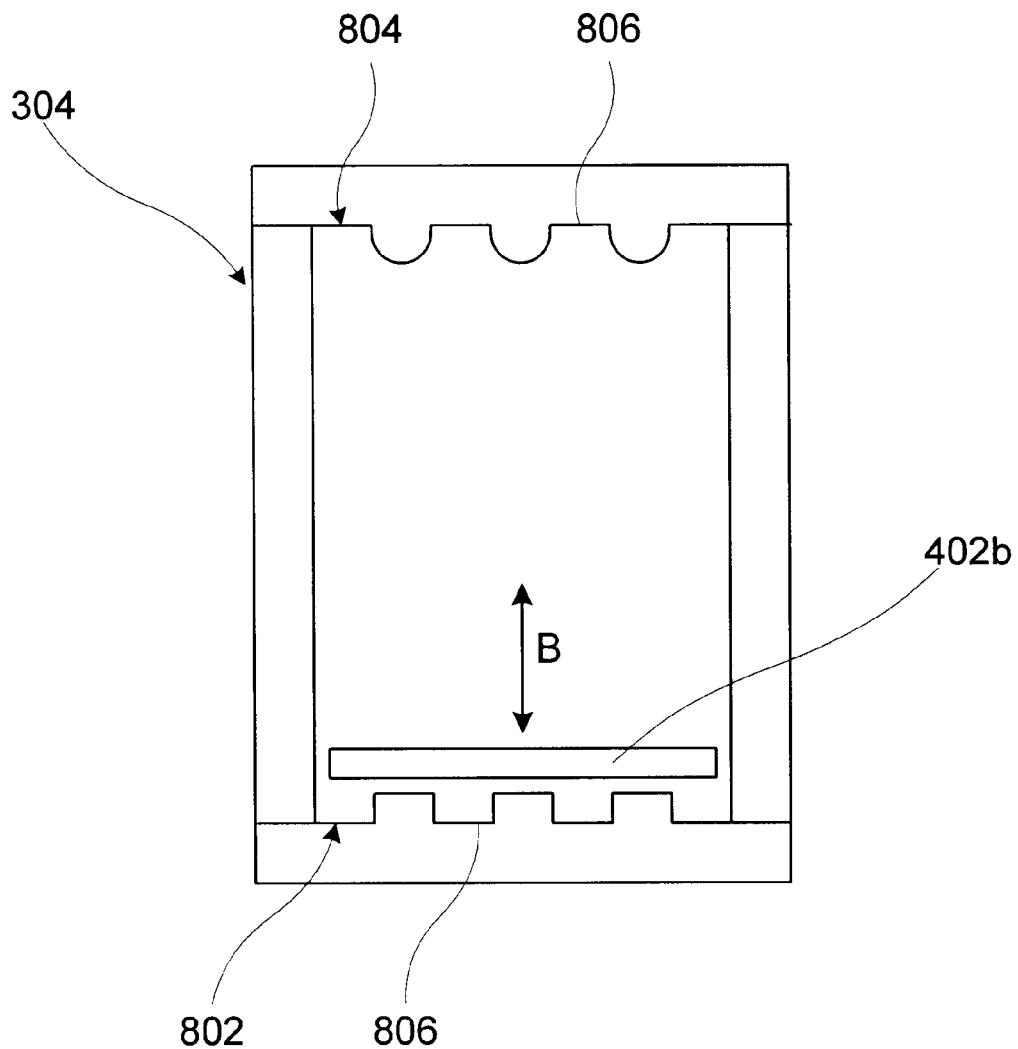
FIG. 8 illustrates an exit end view of a lung vibrating device according to an exemplary embodiment of the present invention.

FIG. 8 illustrates an exit end view of a lung vibrating device according to an exemplary embodiment of the present invention. As shown, the housing 304 can comprise four separate pieces coupled together. The pieces can be coupled together by gluing, sonic welding, taping, or other suitable means. Alternatively, the housing 304 can be molded as a single piece (not shown). The housing 304 can be formed from plastic, wood, metal, or other suitable material.

In an exemplary embodiment, inner surfaces of the housing 304 can comprise a substantially smooth surface (not shown). In the alternative exemplary embodiment illustrated in FIG. 8, a lower inner surface 802 and an upper inter surface 804 of the housing 304 can comprise one or more grooves 806. The grooves 806 reduce the surface area of the inner surfaces 802, 806 of the housing 304 that can contact the reed 402. Accordingly, any condensation that accumulates on the upper and lower inner surfaces 802, 804 of the housing 304 can collect in the grooves 806. The free end 402b of the reed 402 contacts a smaller surface area of the housing 304. Additionally, as shown by the grooves in the upper inner surface 804, the grooves can be rounded to further reduce the surface area contacting the reed 402. In an alternative exemplary embodiment (not shown), the grooves can be pointed to provide a minimum surface area that contacts the reed 402. Thus, the reduced surface area reduces adhesion of the reed 402 to condensation on the inner surfaces 802, 804 of the housing 304.

The grooves 806 also can provide other benefits. For example, the grooves 806 can provide an air path that will tend to lift the reed off the inner surfaces of the housing. Additionally, in an exemplary embodiment, a surface of the grooves can be rough (not shown). Moisture is more likely to condense on the rough surface area in the grooves 806 rather than on the smooth surface area that contacts the reed 402. Accordingly, moisture on the housing surfaces that can contact the reed 402 can be reduced.

The present invention is not limited to the shape of the groove 806 illustrated in FIG. 8. Any suitable shape that reduces the surface area of the housing 304 that contacts the reed free end 402b is within the scope of the present invention. For example, the grooves 806 can comprise a semi-circular shape, a V-shape or other suitable shape. Additionally, the grooves 806 can be provided along the entire length of the housing 304. Alternatively, the grooves 806 can be provided along only a portion of the housing 304, or along intermittent portions of the housing 304. For intermittent portions, the grooves 806 may appear more like individual squares, rectangles, or other shapes in the inner surfaces of the housing 304.

Figure 9A:
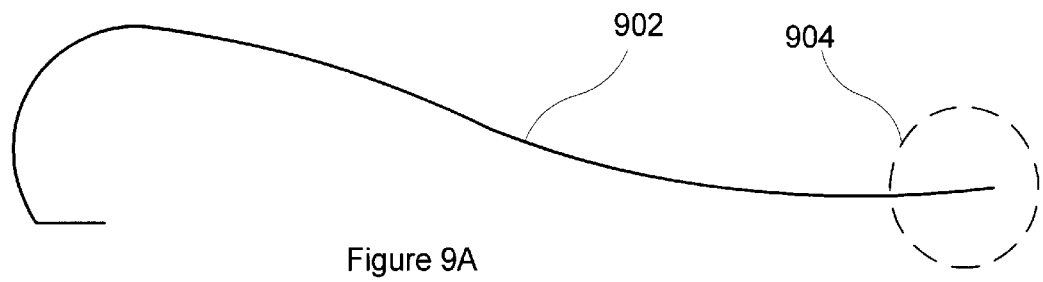
FIG. 9A illustrates a location of a reed weight according to an exemplary embodiment of the present invention.

FIGS. 9A, 9B, 9C, 9D, 9E, and 9F illustrate alternative, exemplary embodiments of a weight provided on a free end 904 of a reed 902. In FIG. 9A, a reed 902 is illustrated. The reed 902 can comprise a reed as described above. A weight can be provided on the reed's free end in the location illustrated by reference numeral 904.

Figure 9B:
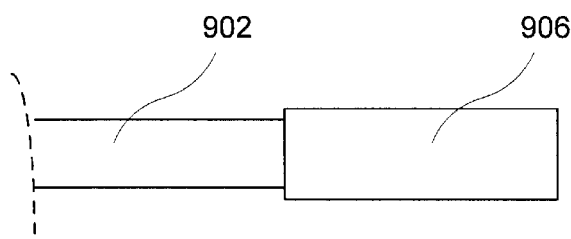
FIG. 9B is a side view illustrating a reed weight according to an exemplary embodiment of the present invention.
Figure 9C:
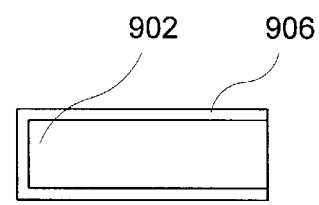
FIG. 9C an end view of the reed weight illustrated in FIG. 9B.

FIG. 9B is a side view illustrating a reed weight 906 according to an exemplary embodiment of the present invention. FIG. 9C is an end view of the reed weight 906 illustrated in FIG. 9B. As shown in FIGS. 9B and 9C, the weight 906 can comprise a weight coupled around the reed 902. In an exemplary embodiment, the weight 906 can comprise tape provided on the end of reed 902.

Figure 9D:
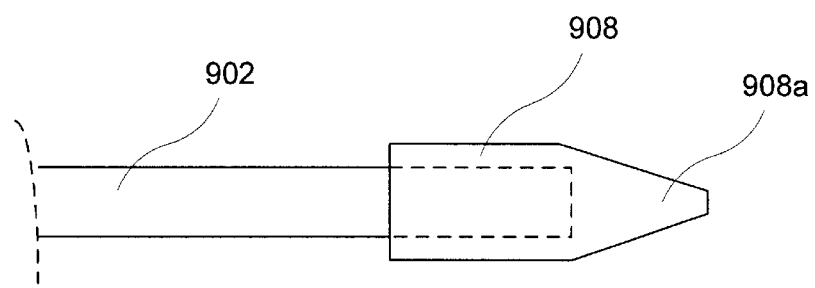
FIG. 9D illustrates an alternative reed weight according to an exemplary embodiment of the present invention.

FIG. 9D illustrates an alternative reed weight 908 according to another exemplary embodiment of the present invention. As shown, the reed weight 908 can envelop the end of the reed 902. Additionally, the reed weight 908 can have a tip end 908a that is tapered. In an exemplary embodiment, the tip end 908a can be thinner than a thickness of the reed 902. The decreased thickness on the tip end 908a can increase the efficiency of the reed 902 to lower the frequency achievable by the reed 902. In an exemplary embodiment, the thinner tip end of reed weight 908 can be provided by using a tape material having the desired thickness. Alternatively, the free end of the reed weight 908 can be tapered by grinding, or notches can be provided in the free end of the reed weight 908 to reduce the surface area of the end of the reed weight 908. In an exemplary embodiment, the reed weight can comprise tape having a thickness of about 0.5 to 1.5 mils. In one exemplary embodiment, the tape can comprise medical tape.

Figure 9E:
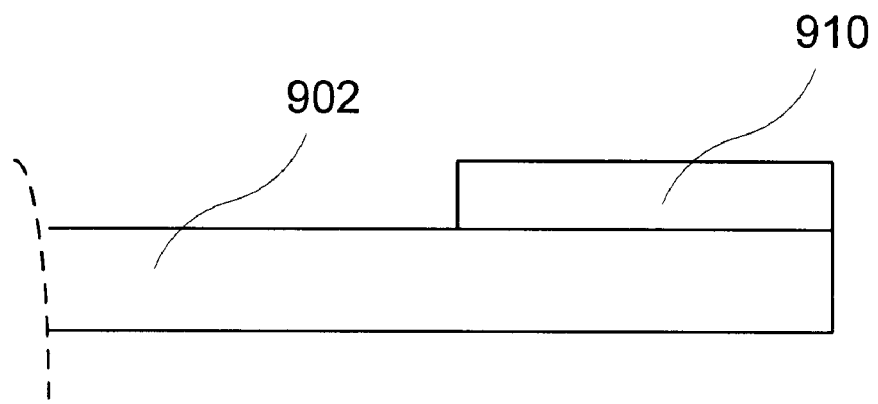
FIG. 9E illustrates a reed weight according to another alternative exemplary embodiment of the present invention.

FIG. 9E illustrates a reed weight 910 according to another alternative exemplary embodiment of the present invention. The reed weight 910 comprises a weight disposed on an end of the reed 902. And that exemplary embodiment, the reed weight can simply increase the thickness and weight of the reed 902 at its free end. In an exemplary embodiment, the reed weight 910 can comprise a material that is the same as the reed 902. In an alternative exemplary embodiment, the reed weight 910 can comprise a material different from the material of the reed, such as tape. In another exemplary embodiment, the free end of the reed/weight combination can be tapered or notched as described above.

Figure 9F:
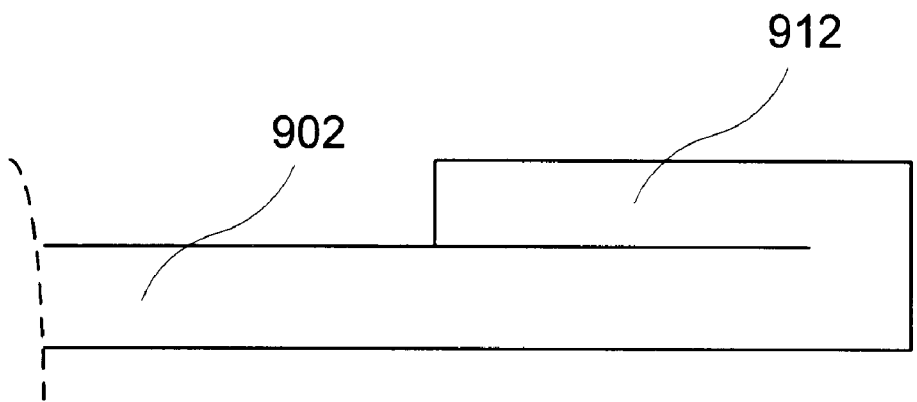
FIG. 9F illustrates a reed weight according to another alternative exemplary embodiment of the present invention.

FIG. 9F illustrates a reed weight 912 according to another alternative exemplary embodiment of the present invention. The reed weight 912 can comprise a double portion of the reed 902. In that regard, the end of reed 902 can be doubled over onto itself to produce the reed weight 912. In an exemplary embodiment, the free end of the reed/weight combination can be tapered or notched as described above.

An area of the end of any reed/weight combination can be reduced to improve the efficiency of the reed 902. The area can be reduced by grinding to taper the end of the reed weight. Alternatively, the area can be reduced by providing grooves or holes in the free end of the weight and reed combination. The grooves or holes remove surface area of the end of the weight, thereby reducing the area.

In an exemplary embodiment, the reed weight can comprise a first material, and the reed can comprise a second material. A compliance of the first material can be in a range of about one-eighth to about one-half of a compliance of the second material. In another exemplary embodiment, the compliance of the first material can be about one-fourth of the compliance of the second material. The differing compliances can increase the efficiency of the reed.

In an exemplary embodiment, the reed can be exchangeable to allow replacement after the reed reaches the end of its useful life. Accordingly, the lung vibrating device can be reconstructed by replacing the reed.

In another exemplary embodiment the reed can comprise, either alone or with a weight, a wear indicator on its free end. The indicator can indicate to a user when the reed has reached its useful life and cannot provide the proper operating frequency. In one embodiment, the reed can comprise an inked indicator that vibrates off over the useful life of the reed.

Figure 10:
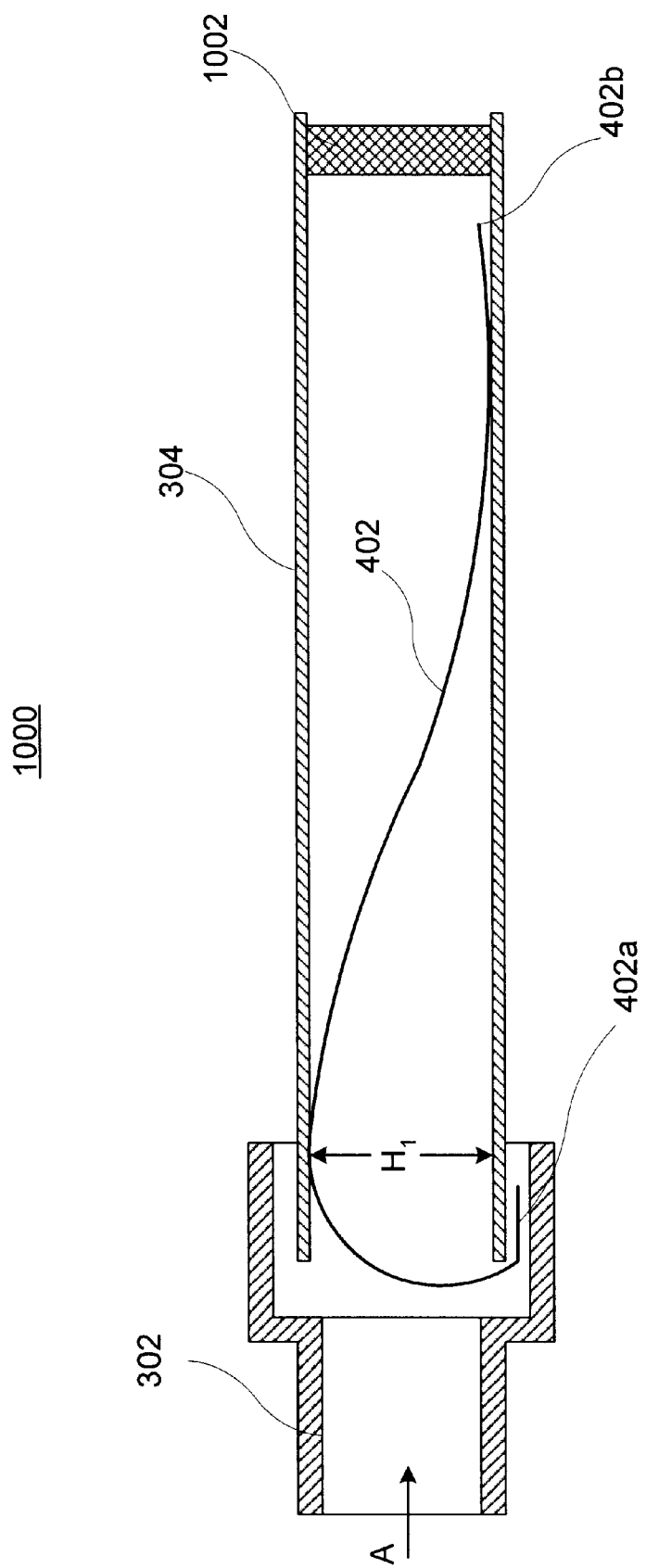
FIG. 10 is a cross-sectional view of a lung vibrating device according to an alternative exemplary embodiment of the present invention.

FIG. 10 is a cross-sectional view of a lung vibrating device 1000 according to another alternative exemplary embodiment of the present invention. As shown, the lung vibrating device 1000 comprises an acoustical resistance plug 1002. The acoustical resistance plug 1002 can comprise a HEPTA filter or a foam plug. Furthermore, the device 1000 can comprise additional acoustical resistances. For example, the device 1000 can comprise an acoustical resistance produced by a size of the reed 402, as described above with reference to FIG. 4. Additionally, or alternatively, the device 1000 can comprise an acoustical resistance composed of an air mass provided in the housing 304, as described above with reference to FIG. 4.

Figure 11:
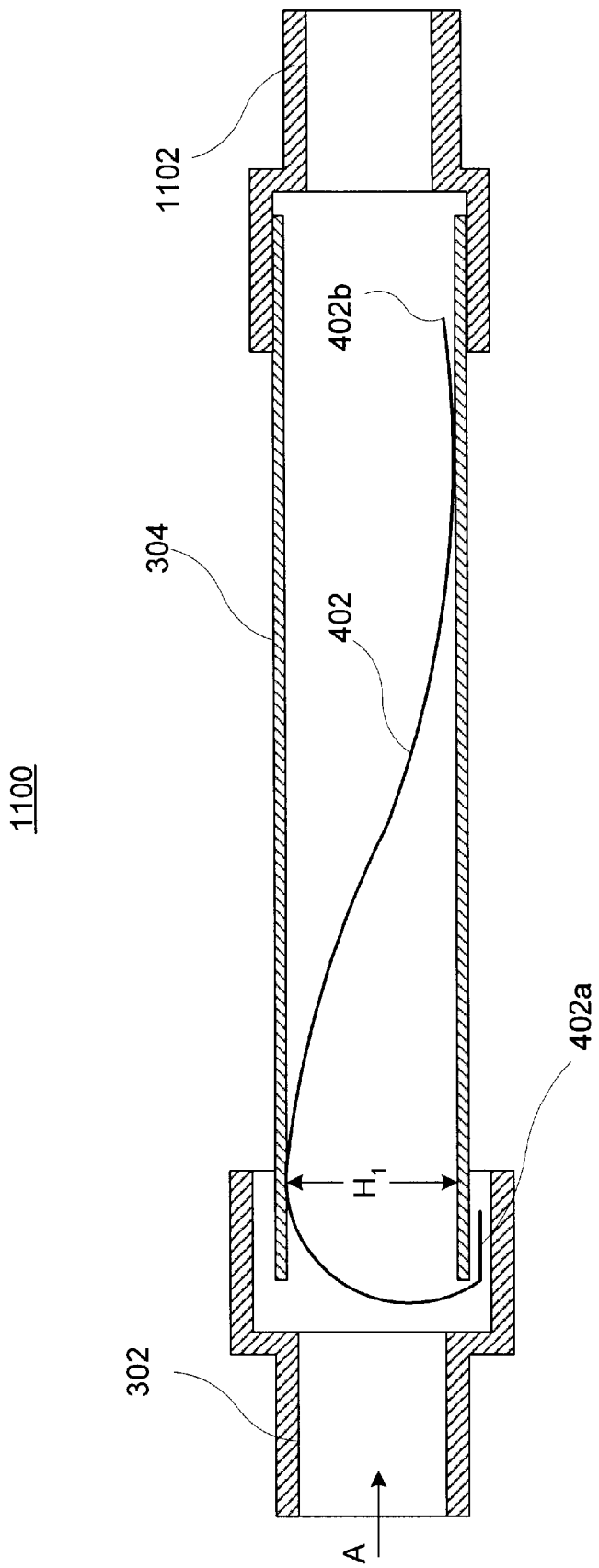
FIG. 11 is a cross-sectional view of a lung vibrating device according to another alternative exemplary embodiment of the present invention.

FIG. 11 is a cross-sectional view of a lung vibrating device 1100 according to another alternative exemplary embodiment of the present invention. As shown, the lung vibrating device 1100 can comprise a second end cap 1102 provided on the housing 304. The second end cap 1102 can function as an acoustical resistance by restricting the air flow from the housing 304. Additionally, the second end cap 1102 can provide a means to connect the device 1100 to a respirator. In an alternative exemplary embodiment, the second end cap 1102 can provide a means to connect the device 1100 to a respirator without serving as an acoustical resistance. When connected to a respirator, the respirator can draw air through the housing 304 to drive the reed 402 to produce the acoustical shockwave in the patient's lungs.

Figure 12:
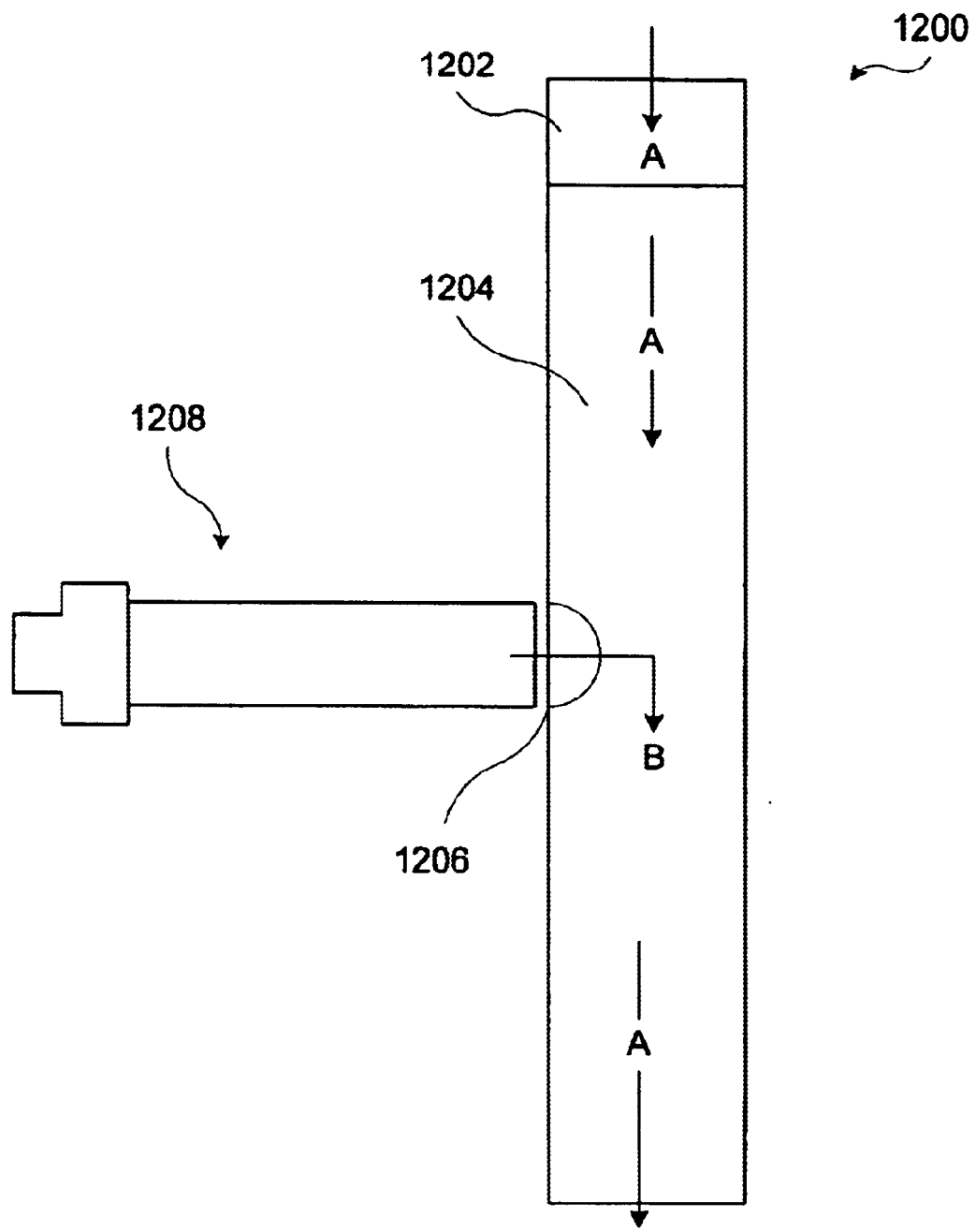
FIG. 12 is a block diagram illustrating an exemplary power make up device for a lung vibrating device according to an exemplary embodiment of the present invention.

FIG. 12 is a block diagram illustrating an exemplary power make up device 1200 for a lung vibrating device according to an exemplary embodiment of the present invention. As shown, a fan 1202 can push air through a duct 1204 in the direction of the arrows A. The duct 1204 can comprise an aperture 1006. An exit opening of a lung vibrating device 1208 can be provided in proximity to the aperture 1206. The air moving in the direction A within the duct 1204 can draw air in the direction B through the lung vibrating device 1208. Accordingly, the power make up device 1200 can produce at least a partial vacuum in the lung vibrating device 1208 by drawing air from the lung vibrating device 1208 in the direction of the arrow B. In an exemplary embodiment, the device 1200 can produce about 1.5 inches of negative water pressure in the lung vibrating device 1208.

As evident to those skilled in the art, the lung vibrating device according to the present invention can incorporate many features not illustrated in the attached figures. For example, exemplary embodiments can comprise a space-saving design, incorporating a foldable, hinged, or telescoping housing. Another embodiment encompasses a device formed from a thin material that can be crumpled and disposed.

The lung vibrating device can be used to perform many functions. For example, the device can be used to induce sputum to clear the lungs or to provide a diagnostic sample, improve muscillary clearance post operatively, prevent lung collapse (atelectasis), improve oxygenation, improve lung capacity or lung clearance in athletes prior to performance, or treat smoke inhalation.

The efficient coupling of an audio source and a body cavity to produce low-frequency sound can be used for other applications. The acoustical resistance can be adjusted to provide the proper frequency based on the particular application. Additionally, the reed can be tuned by changing its size, shape, or material to provide the proper frequency. For example, other applications can include the following:

Coronary Plaque: One application can be erosion of coronary arterial plaque by vibration. An adaptation of the powered system may erode coronary arterial plaque by internal thoracic vibration, which would be a useful clinical application.

Sinus and Ear: Several variations of the powered and non-powered lung cleaning systems can be used for sinus drainage and middle ear clearing. Operation requires a simple frequency adjustment of the lung cleaning system by an adjustment of the acoustical resistance. For uses such as sinus drainage and middle ear clearing, the systems can operate in a range between about 15 Hz and about 60 Hz with an output of from about 75 dBa to about 100 dBa. The systems also can operate between about 40 Hz and about 60 Hz, and at about 44 Hz.

Diagnostics: A lung vibrating device according to the present invention can provide the basis of a sophisticated diagnostic tool for lung diseases such as pneumonia, COPD, asthma, and lung cancer. The diagnostic system can monitor the voltage to current phase of the loudspeaker motor and then derive the dynamic compliance of the lungs at different frequencies and different pressures and vacuums. Lung compliance varies with different secretion loads and also shows changes in elasticity caused by long term lung tissue deterioration. Accordingly, the results can be correlated with existing conditions. Early asymptomatic results also can be correlated with later disease conditions.

Intestines/Colon: Another application is to efficiently couple a patient's colon to an audio source to clean the patient's intestines or colon. That application can remove intestinal blockages, which can prevent such blockages from causing a dangerous infection.

Although specific embodiments of the present invention have been described above in detail, the description is merely for purposes of illustration. Various modifications of, and equivalent steps corresponding to, the disclosed aspects of the exemplary embodiments, in addition to those described above, can be made by those skilled in the art without departing from the spirit and scope of the present invention defined in the following claims, the scope of which is to be accorded the broadest interpretation so as to encompass such modifications and equivalent structures.

What is claimed is:

1. A method for thinning lung secretions, comprising the steps of:
   blowing an air mass trough a housing of a lung device;
   vibrating a reed disposed in the housing via air flow past the reed to produce low-frequency sound in a range of about 12 Hz to about 24 Hz; and
   providing an acoustical resistance in the housing that slows an air flow rate within the housing to couple the air mass in the housing to an air mass in a lung cavity of a patient's lungs, thereby creating a virtual air cavity comprising a virtual air mass that is larger than the air mass in the housing,
   wherein the low-frequency sound vibrates the air mass in the virtual air cavity, thereby vibrating the patient's lungs to thin lung secretions.

2. The method according to claim 1, wherein the acoustical resistance provided in said providing step comprises one of a filter and a foam plug in the housing.

3. The method according to claim 1, wherein the acoustical resistance provided in said providing step comprises a tapered end of the housing which restricts air flow from the housing.

4. The method according to claim 1, wherein the acoustical resistance provided in said providing step comprises an end cap disposed on an end of the housing that restricts air flow from the housing.

5. The method according to claim 1, wherein the acoustical resistance provided in said providing step comprises a volume of the housing that encompass an air mass large enough to produce the acoustical resistance.

6. The method according to claim 1, wherein the acoustical resistance provided in said providing step comprises a size of the reed which slows the air flow rate within the housing.

7. The method according to claim 1, further comprising the step of preventing the reed from adhering to a top inner surface and a bottom inner surface of the housing while the reed vibrates within the housing.

8. The method according to claim 1, further comprising the step of improving the efficiency of said vibrating step by providing a weight on a free end of the reed.

9. The method according to claim 1, further comprising the step of producing at least a partial vacuum in the housing to assist in said vibrating step.

10. The method according to claim 1, further comprising the step of harvesting a sputum sample from the thinned lung secretions.

11. A device for thinning lung secretions, comprising:
    a housing encompassing an air mass flowing through said housing when a patient blows air into said housing;
    a reed disposed in said housing, said reed producing low-frequency sound in a range of about 12 Hz to about 24 Hz when vibrated by the air mass flowing through said housing; and
    an acoustical resistance that couples the air mass in said housing to an air mass in a lung cavity of the patient to create a virtual air cavity comprising a virtual air mass that is larger than the air mass in said housing, the virtual air cavity assisting said reed to produce the low-frequency sound,
    wherein the low-frequency sound vibrates the air mass in the virtual air cavity thereby vibrating the patient's lung cavity to thin lung secretions.

12. The device according to claim 11, wherein said acoustical resistance comprises a filter disposed in said housing.

13. The device according to claim 11, wherein said acoustical resistance comprises a foam plug disposed in said housing.

14. The device according to claim 11, wherein said acoustical resistance comprises a tapered end of said housing that restricts air flow from said housing.

15. The device according to claim 11, wherein said acoustical resistance comprises an end cap disposed on an end of said housing that restricts air flow from said housing.

16. The device according to claim 1, wherein said acoustical resistance comprises the air mass flowing through said housing, and
    wherein said housing comprises a volume sufficient to encompass an air mass large enough to produce said acoustical resistance.

17. The device according to claim 11, wherein said acoustical resistance comprises a size of said reed that provides resistance to air flow within said housing.

18. The device according to claim 11, wherein said device comprises a plurality of acoustical resistances that couple the air mass in said housing to the air mass in the patient's lungs.

19. The device according to claim 18, wherein said plurality of acoustical resistances comprises a size of said reed and the air mass flowing through said housing.

20. The device according to claim 11, wherein said low-frequency sound comprises a frequency in a range of about 16 Hz to about 20 Hz.

21. The device according to claim 20, wherein said low-frequency sound comprises a frequency of about 18 Hz.

22. The device according to claim 11, further comprising a mouthpiece coupled to said housing, wherein the patient blows air into said housing through said mouthpiece.

23. The device according to claim 22, wherein said reed is coupled to said housing by being coupled to said mouthpiece which is coupled to said housing.

24. The device according to claim 22, wherein an end of said housing is disposed within said mouthpiece to couple said mouthpiece to said housing, and wherein said reed is coupled to said housing by having an end of said reed compressed between said housing and said mouthpiece.

25. The device according to claim 24, wherein one of said housing and said mouthpiece comprises a positioning channel that positions said reed within said housing.

26. The device according to claim 11, wherein said housing comprises a first portion having a first cross-sectional area and a second portion having a second cross-sectional area, and wherein said second cross-sectional area is larger than said first cross-sectional area.

27. The device according to claim 26, wherein said reed comprises a free end, and wherein said free end vibrates within the second portion of said housing.

28. The device according to claim 11, wherein said housing comprises an inner surface having a groove formed therein, wherein said reed intermittently contacts the inner surface of said housing during vibration of said reed.

29. The device according to claim 28, wherein said housing comprises a top inner surface and a bottom inner surface, and wherein said groove is disposed in one of the top and bottom inner surfaces.

30. The device according to claim 29, wherein said housing comprises a plurality of grooves disposed in at least one of the top and bottom inner surfaces.

31. The device according to claim 11, wherein said reed comprise a free end, and wherein said free end comprises a cross-sectional area that is smaller than a cross-sectional area of another portion of said reed.

32. The device according to claim 11, wherein said reed comprises a free end, and wherein said reed further comprises a weight disposed on the free end of said reed.

33. The device according to claim 32, wherein said weight comprises a free end having a cross-sectional area that is smaller than a cross-sectional area of a portion of said reed.

34. The device according to claim 32, wherein a portion of said weight and said reed comprises a cross-sectional area that is smaller than a cross-sectional area of another portion of said weight and said reed.

35. The device according to claim 32, wherein said weight comprises a first material and said reed comprises a second materials, and wherein a compliance of the first material is in a range of about one-eighth to about one-half of a compliance of the second material.

36. The device according to claim 32, wherein said weight comprises a double portion of said reed.

37. The device according to claim 32, wherein said weight comprises tape coupled to the free end of said reed.

38. The device according to claim 11, further comprising a power makeup device coupled to said housing for creating at least a partial vacuum in said housing.

39. The device according to claim 34, wherein said housing comprises an exit opening, and wherein said power makeup device comprises an air flow past the exit opening of said housing.

40. The device according to claim 11, wherein said housing comprises a first end and a second end, and wherein said device further comprises a first respirator tube coupled to the first end of said housing to couple said device to a respirator.

41. The device according to claim 40, further comprising a first end cap coupled to the first end of said housing, wherein said first respirator tube is coupled to said first end cap.

42. The device according to claim 40, wherein said device further comprises a second respirator tube coupled to the second end of said housing to couple said device to the patient.

43. The device according to claim 11, wherein said acoustical resistance couples the air mass in said housing to the air mass in the patient's lungs by slowing a flow rate of the air mass flowing through said housing.

44. A device for thinning lung secretions, comprising:

a housing having an end adapted to receive air from a patient;

a reed comprising a fixed end coupled to said housing and a free end disposed within said housing, said reed further comprising a weight disposed on said free end, and said reed producing a low-frequency acoustical shockwave in a range of about 12 Hz to about 24 Hz when vibrated by air flowing through said housing; and at least one acoustical resistance that reduces a flow rate of air through said housing to couple the low-frequency acoustical shockwave to a lung cavity of the patient, thereby vibrating the patient's lung cavity to thin lung secretions.

45. The device according to claim 46, wherein said acoustical resistance comprises a filter disposed in said housing.

46. The device according to claim 46, wherein said acoustical resistance comprises a foam plug disposed in said housing.

47. The device according to claim 46, wherein said acoustical resistance comprises a tapered end of said housing.

48. The device according to claim 46, wherein said acoustical resistance comprises an end cap disposed on an end of said housing to restrict air flow from said housing.

49. The device according to claim 46, wherein said acoustical resistance comprises an air mass flowing through said housing, and wherein said housing comprises a volume sufficient to encompass an air mass large enough to produce said acoustical resistance.

50. The device according to claim 44, wherein said acoustical resistance comprises a size of said reed that reduces the flow rate of air through said housing.

51. The device according to claim 44, wherein said shockwave comprises a frequency in a range of about 16 Hz to about 20 Hz.

52. The device according to claim 44, further comprising a mouthpiece coupled to said housing, wherein said reed is coupled to said housing by having said fixed end compressed between said housing and said mouthpiece.

53. The device according to claim 44, further comprising a mouthpiece coupled to said housing, wherein said reed is coupled to said housing by being coupled to said mouthpiece which is coupled to said housing.

54. The device according to claim 44, wherein said fixed end of said reed is coupled to said housing at a first portion of said housing, wherein said free end of said reed vibrates within a second portion of said housing, and wherein the second portion comprises a larger cross-sectional area than the first portion.

55. The device according to claim 44, wherein said housing comprises an inner surface having at least one groove formed therein, wherein said free end of said reed intermittently contacts the inner surface of said housing during vibration of said reed.

56. The device according to claim 44, wherein said weight comprises a free end, and wherein the free end of said weight is thinner than a thickness of said reed.

57. The device according to claim 56, wherein said weight comprises a first material and said reed comprises a second material, and wherein a compliance of the first material is in a range of about one-eighth to about one-half of a compliance of the second material.

58. The device according to claim 44, further comprising a power makeup device coupled to said housing that creates at least a partial vacuum in said housing.

59. A device for lowering the viscosity of human secretions, comprising:

a housing encompassing an air mass flowing therethrough;

a reed disposed in said housing, said reed producing a low-frequency sound shockwave in a range of about 15 Hz to about 60 Hz when vibrated by the air mass flowing through said housing; and an acoustical resistance that couples the air mass in said housing to an air mass in a body cavity of a patient to create a virtual air cavity comprising a virtual air mass that is larger than the air mass in said housing, wherein the low-frequency sound shockwave vibrates the air mass in the virtual air cavity, thereby vibrating the patient's body cavity to thin secretions contained therein.

60. The device according to claim 59, wherein said shockwave comprises a frequency in a range of about 16 Hz to about 20 Hz.

61. The device according to claim 59, wherein said shockwave comprises a frequency of about 44 Hz.

62. The device according to claim 59, wherein the body cavity comprises a sinus cavity.

* * * * *

UNITED STATES PATENT AND TRADEMARK OFFICE
CERTIFICATE OF CORRECTION

PATENT NO.    : 6,702,769 B1               Page 1 of 1
DATED         : March 9, 2004
INVENTOR(S)   : Sanford Elliot Fowler-Hawkins It is certified that error appears in the above-identified patent and that said Letters Patent is hereby corrected as shown below:

Column 11,
Line 36, "trough" should read -- through --.
Line 62, "encompass" should read -- encompasses --.

Column 12,
Line 41, "claim 1" should read -- claim 11 --.

Column 13,
Line 51, "materials" should read -- material --.
Line 62, "claim 34" should read -- claim 38 --.

Column 14,
Lines 30, 33, 36, 39 and 42, "claim 46" should read -- claim 44 --.

Signed and Sealed this

First Day of June, 2004

JON W. DUDAS
*Acting Director of the United States Patent and Trademark Office*